US008871270B2

(12) United States Patent
Zhang et al.

(10) Patent No.: US 8,871,270 B2
(45) Date of Patent: Oct. 28, 2014

(54) TABLET EXCIPIENT

(75) Inventors: Yeli Zhang, Somerville, NJ (US); Chaodong Xiao, East Hanover, NJ (US); Wolfgang Bindzus, Hillsborough, NJ (US); Vincent Green, Plainfield, NJ (US)

(73) Assignee: Corn Products Development, Inc, Jabaquara, Sao Paulo (BR)

( * ) Notice: Subject to any disclaimer, the term of this patent is extended or adjusted under 35 U.S.C. 154(b) by 1630 days.

(21) Appl. No.: 10/888,360

(22) Filed: Jul. 9, 2004

(65) Prior Publication Data
US 2006/0008521 A1    Jan. 12, 2006

(51) Int. Cl.
*A61K 9/14* (2006.01)
*A61K 47/36* (2006.01)
*A61K 9/20* (2006.01)

(52) U.S. Cl.
CPC .............. *A61K 47/36* (2013.01); *A61K 9/2059* (2013.01)
USPC .......................................... 424/489; 424/493

(58) Field of Classification Search
USPC ................... 424/361, 484, 489, 493
See application file for complete search history.

(56) References Cited

U.S. PATENT DOCUMENTS

| | | | |
|---|---|---|---|
| 3,490,742 A | 1/1970 | Nichols et al. | |
| 3,622,677 A | 11/1971 | Short et al. | |
| 4,072,535 A * | 2/1978 | Short et al. | 106/206.1 |
| 4,369,308 A | 1/1983 | Trubiano | |
| 4,383,111 A | 5/1983 | Takeo et al. | |
| 4,551,177 A | 11/1985 | Trubiano et al. | |
| 5,164,014 A | 11/1992 | Brancq et al. | |
| 5,374,687 A | 12/1994 | Cooperman et al. | |
| 5,468,286 A | 11/1995 | Wai-Chiu et al. | |
| 5,616,343 A | 4/1997 | Cartilier et al. | |
| 6,143,324 A | 11/2000 | Michaud et al. | |
| 6,184,213 B1 | 2/2001 | Lefevre et al. | |
| 6,455,069 B1 | 9/2002 | Michaud et al. | |
| 2002/0054905 A1 * | 5/2002 | Weisser et al. | 424/465 |
| 2003/0141637 A1 * | 7/2003 | Kesselmans et al. | 264/555 |
| 2006/0008521 A1 | 1/2006 | Zhang et al. | |

FOREIGN PATENT DOCUMENTS

EP     1 443 057 A1    8/2004

OTHER PUBLICATIONS

Brummer, Thomas—XP-002438016—Expansion and Functional Properties of Corn Starch Extrudates Related . . . Starch/Starke vol. 54 (2002), pp. 9-15.
Tamime, Robinson—Yoghurt: Science and Technology, 1985, Pergamon Press Ltd. UK, 1st Ed. Chapters 2 and 5.

\* cited by examiner

*Primary Examiner* — Michael G Hartley
*Assistant Examiner* — Micah-Paul Young
(74) *Attorney, Agent, or Firm* — Karen G. Kaiser

(57) ABSTRACT

This invention relates to a composition comprising physically modified, partially pregelatinized starch, which is useful as a multi-functional excipient for solid dosage forms, a method of making such composition, and solid dosage forms prepared using the composition. Such composition is characterized by a predominance of particles having both birefringent and non-birefringent portions, a sedimentation volume of between 1.5 and 9 ml/g, and a cold water solubility of between 1 and 8%. This free-flowing starch may have an average particle size greater than 30 µm, and a moisture content of between 5 and 12% by weight. The 500 mg placebo tablet prepared from such composition at 13 kN using a manual tablet press equipped with a 1.11 cm (7/16") standard concave punches has a crushing strength of at least 160 Newtons, and a disintegration time of no more than 10 minutes.

16 Claims, 7 Drawing Sheets

US 8,871,270 B2

TABLET EXCIPIENT

FIELD OF THE INVENTION

This invention relates to a composition comprising physically modified partially pregelatinized starch, which is useful as a multi-functional excipient for solid dosage forms, a method of making such composition, and solid dosage forms prepared using the composition.

There is a need for multi-functional starch excipients which exhibit excellent compression profiles, good disintegration and dissolution properties and excellent flowability. Such starch excipients should be neither chemically modified nor enzymatically treated.

SUMMARY OF THE INVENTION

This invention relates to a physically modified, partially pregelatinized starch composition which is useful as a multi-functional excipient for solid dosage forms. It is characterized by a predominance of particles having both birefringent and non-birefringent portions, wherein the birefringent portions may be bonded together by the non-birefringent portions, a sedimentation volume of between 1.5 and 9 ml/g, and a cold water solubility of between 1 and 8%. This free-flowing starch typically has an average particle size greater than 30 µm, and a moisture content of between 5 and 12% by weight. The 500 mg placebo tablet prepared from such composition at 13 kN using a manual tablet press equipped with a 1.1 cm standard concave punches has a crushing strength of at least 160 N, and a disintegration time of no more than 10 minutes.

At least partially gelatinized, as used herein, is intended to mean that the starch particles have portions which are gelatinized, evidenced by no birefringence and the full destruction of the Maltese cross, and portions which are not gelatinized, evidenced by birefringence and the presence of the Maltese cross.

Birefringent (birefringence), as used herein, is intended to mean that the non-pregelatinized starch granules have birefringence under polarized light. This is shown by the presence of a Maltese cross, either full or partial.

Physically modified, as used herein, is intended to mean that the starch is mechanically altered, but is not chemically or enzymatically modified.

Sedimentation volume (SV), as used herein, is intended to mean the volume of sediment of 1 gram of starch in 99 grams of water at 25° C. using the test defined in the Examples section.

Cold water solubility (CWS), as used herein, is intended to mean the percent by weight of the starch which dissolves in water at 25° C. using the test defined in the Examples section.

Filler or diluent, as used herein, is intended to mean inert ingredients used to decrease the concentration of the active ingredient in the final formulation.

Binder, as used herein, is intended to mean an ingredient used to hold or help to hold together the structure of the dosage form. Binders have the property to hold together the other ingredients after sufficient compression forces have been applied.

Disintegrant, as used herein, is intended to mean an ingredient which helps the dosage form disintegrate when placed in a liquid environment.

Solid dosage form, as used herein, is intended to include, without limitation, tablets, caplets, powders and dry dosage capsules.

Crushing strength, as used herein, is intended to mean the force necessary to fraction the dosage form using the test defined in the Examples section.

Disintegration time, as used herein, is intended to mean the amount of time a solid dosage form takes to lose its full structural integrity using the test defined in the Examples section.

The starch composition according to this invention is a multi-functional excipient, which possesses excellent binding, disintegrating, and flow properties. It is also capable of accelerating drug dissolution from a solid dosage form.

DETAILED DESCRIPTION OF THE INVENTION

Figure 1:
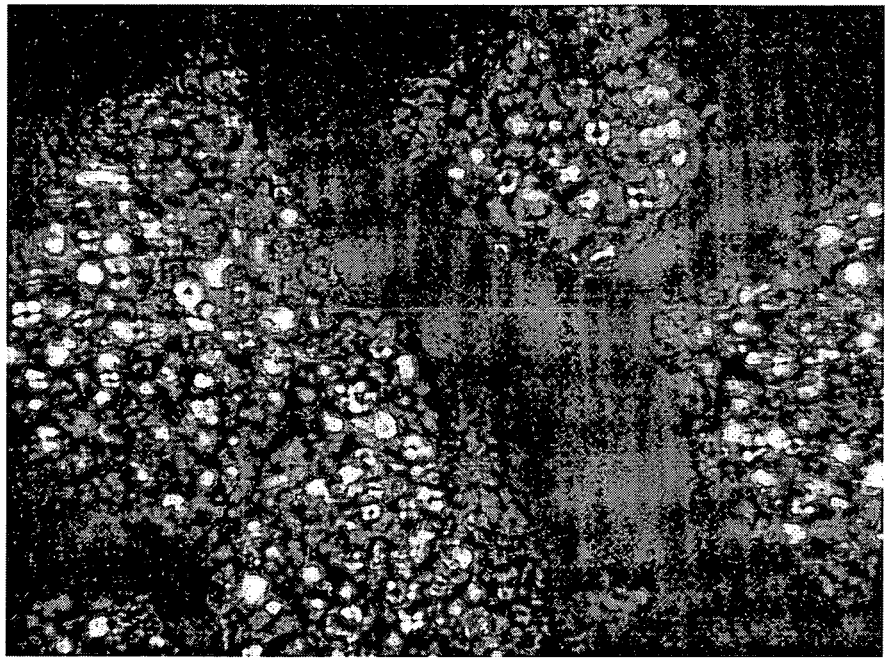
FIG. 1 depicts a photomicrograph, taken under polarized light, of extruded corn starch at a magnification of 200.

This invention relates to a composition comprising partially pregelatinized starch, which is useful as a multi-functional excipient for solid dosage forms, a method of making such composition, and solid dosage forms prepared using the composition.

All starches and flours (hereinafter "starch") may be suitable for use as base materials herein and may be derived from any native source. A native starch as used herein, is one as it is found in nature. Also suitable are starches derived from a plant obtained by standard breeding techniques including crossbreeding, translocation, inversion, transformation or any other method of gene or chromosome engineering to include variations thereof. In addition, starch derived from a plant grown from artificial mutations and variations of the above generic composition, which may be produced by known standard methods of mutation breeding, are also suitable herein. Typical sources for the starches are cereals, tubers, roots, legumes and fruits. The native source can be corn, pea potato, sweet potato, banana, barley, wheat, rice, sago, oat, amaranth, tapioca, arrowroot, canna, sorghum, and waxy or high amylose varieties thereof. As used herein, the term "waxy" is intended to include a starch containing at least about 90%, particularly at least 95%, more particularly at least 98, most particularly at least 99%, by weight amylopectin and the term "high amylose" is intended to include a starch containing at least about 40%, particularly at least 50%, more particularly at least 70%, most particularly at least 80%, by weight amylose. In one aspect of this invention, amylose-containing starch extracted from cereal grains, such as corn, are used. In another aspect of this invention, blends of starches are used, such as a blend of corn starch and high amylose corn starch.

The starch is prepared by physical processing, which includes without limitation extrusion, pre-compaction, cooking of a starch slurry, spray drying, and fluidized bed agglomeration. In one embodiment, such processing is by extrusion. The starch is treated so as to partially pregelatinize the starch, and create starch particles with gelatinized and non-gelatinized portions. In one embodiment, the gelatinized starch essentially binds the non-gelatinized particles (ie. granules) together.

Extrusion may be conducted using any suitable equipment and process parameters known in the art. Since a large number of combinations of process parameters exist, e.g., product moisture, screw design and speed, feed rate, barrel temperature, die design, formula and length/diameter (L/d) ratios, Specific Mechanical Energy (SME) and Product Temperature (PT) have been used in the art to describe the process parameter window of the extrusion. In one embodiment, the starch is prepared by extrusion cooking at a product temperature of 50 to 110° C. In another embodiment, the starch is prepared by extrusion cooking at a product temperature of 85 to 95° C. In one embodiment, the starch is prepared by extrusion cooking at an SME of less than 210 Wh/kg. In another embodiment, the SME is from 120 to 180 Wh/kg. Beyond SME and PT, it is important to describe the moisture range, which influences the starch melting characteristics and the residence time, in the context of extrusion described by screw chamber length-over-diameter ratio (L/d-ratio). In one embodiment, the moisture content is between 20 and 35%, in another, between 30 and 35%, with a length to diameter ratio (L/d) of 9 or less. For such a design, the residence time in one embodiment is less than 20 seconds.

The resulting composition will be in the form of starch pellets. It is then dried and ground to a particle size compatible with the particle size of the other tableletting components. In one embodiment, the starch is ground to a particle size such that at least 99% passes through a 40 mesh screen (opening of 425 microns). In another embodiment, a median particle size range for direct compression application is in the range of 40 to 150 µm, and in another embodiment is between 60 and 100 µm.

Figure 2:
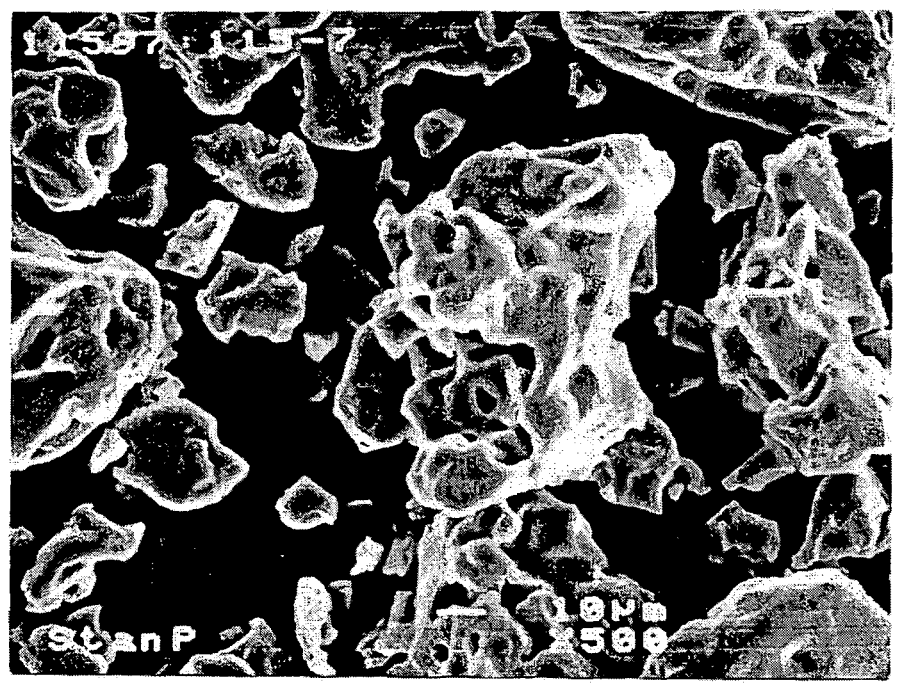
FIG. 2 depicts a scanning electron microphotograph of extruded corn starch useful in accordance with the present invention, at a magnification of 500.

A majority of the particles of this multi-functional starch composition include both birefringent and non-birefringent portions. The birefringent portions may be bonded together by the non-birefringent portions and form a strong particle. Therefore, a majority of the particles of this starch composition will be typically much larger than a single starch granule both in dry form and after dispersion in water (FIGS. 1 and 2).

The particle strength of the multi-functional starch composition disclosed in this invention is strong. Particle strength is important in terms of determining the basic properties of the powder, such as segregation, flow, and density. Strong particles are more apt than weak particles to survive mechanical stress. Particle strength was tested using the ultrasonic technique defined in the Examples section. Briefly, after dispersing the composition in water and applying ultrasonic vibration for a total of 6 minutes, the majority of particles are still larger than a single starch granule. In one embodiment, at least 90% of the particles will have a particle size of greater than 20 µm (the size of an individual starch granule in water). The particle size reduction rate of the composition is close to that of native starch granules (1 µm/min) using the test described in the Examples section, and in one aspect of the invention is about 2 µm/min.

The multi-functional starch composition will have a sedimentation volume of between 1.5 and 9 ml/g. In one embodiment, the sedimentation volume will be between 3 and 6 ml/g.

The starch composition will also have a cold water solubility of between 1 and 8%. In one embodiment, the cold water solubility will be between 2 and 5%. This free-flowing starch may have an average particle size greater than 30 µm. In one embodiment, the starch will have an average particle size between 40 and 150 µm, and in another embodiment in the range of 60 to 100 µm. The starch may have a moisture content of from 5 to 12% by weight. In one embodiment, the moisture content of the starch will be between 8 and 10%.

Placebo tablets obtained from partially pregelatinized starch with such sedimentation volume are characterized by the fact that they show significantly higher hardness at any given compression force than starches having a sedimentation volume outside of this range. At the same time, such placebo tablets will disintegrate in an aqueous medium at significantly higher speed than placebos prepared with starches having a sedimentation volume outside of this range. In addition, when such starch is used as a filler or diluent inside a hardgel capsule, an increased drug dissolution rate is observed compared to other starches having a sedimentation value outside this range.

The 500 mg placebo tablet, with a moisture content of at least 7%, prepared from such multi-functional starch composition at 13 kN compression force using a manual tablet press equipped with a 1.11 cm standard concave punches may have a crushing strength of at least 160 N. In one embodiment the crushing strength will be at least 180 N; in another embodiment at least 200 N. The disintegration time of such tablets may be no more than 10 minutes. In one embodiment, the disintegration time will be no more than 8 minutes, and in another embodiment, no more than 5 minutes.

The multi-functional starch composition shows excellent flowability as evidenced by a mean time for avalanche (MTA) of no more than 10 seconds. In one embodiment, the MTA is no more than 7 seconds.

The multi-functional starch composition's particle size and moisture content will affect the powder's flowability, density, compressibility, binding, and disintegration properties. By controlling the particle size and moisture content, the powder's flowability, density, compressibility, binding, and disintegration property may be controlled and tailored to satisfy different application requirements.

The multi-functional starch composition may be used as an excipient in solid dosage forms, including without limitation, capsules, caplets, and tablets.

The multi-functional starch composition may be incorporated into a solid dosage form using methods known in the art. In one embodiment, the starch composition is mixed with the active agent and filled into a capsule.

In another embodiment, the multi-functional starch composition is incorporated using direct compression, a process by which the starch composition is mixed with the active agent and other ingredients, which mixture is capable of flowing uniformly into a die cavity, and is compressed directly into an acceptable dosage form, such as a tablet. The advantages of direct compression include limiting exposure of the active material to moisture and/or heat, and long-term physical and chemical stability. Direct compression requires only two steps, mixing the dry ingredients and compressing the mixture to a tablet, and hence it is currently the most commonly used method in the pharmaceutical industry as well as an economical method of tabletting.

Figure 4:
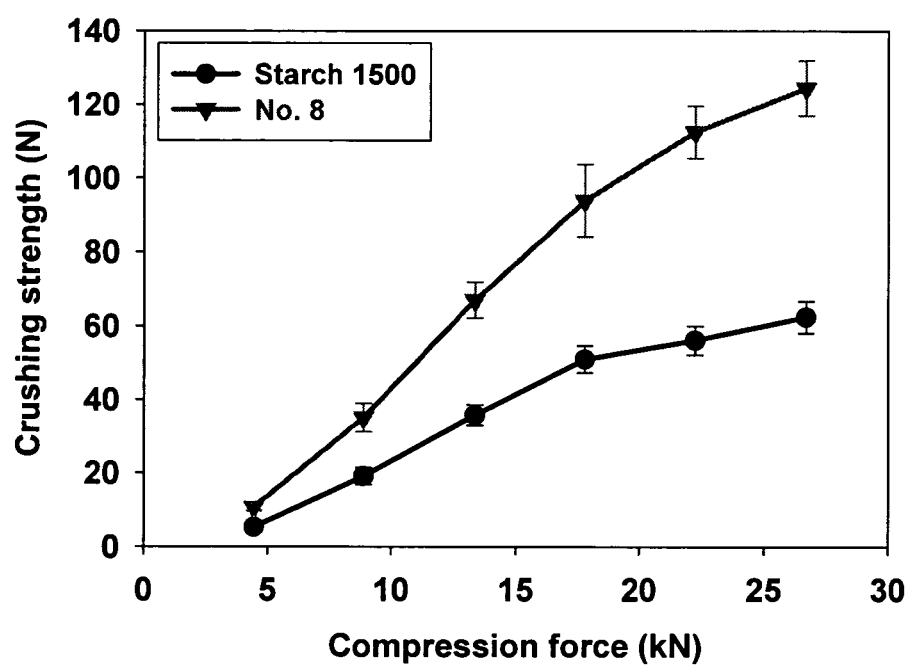
FIG. 4 depicts the compaction profile of hydrocholothiazide (HCTZ) tablets prepared according to Tableletting Procedure 2 using the test defined in the Examples section.
Figure 5:
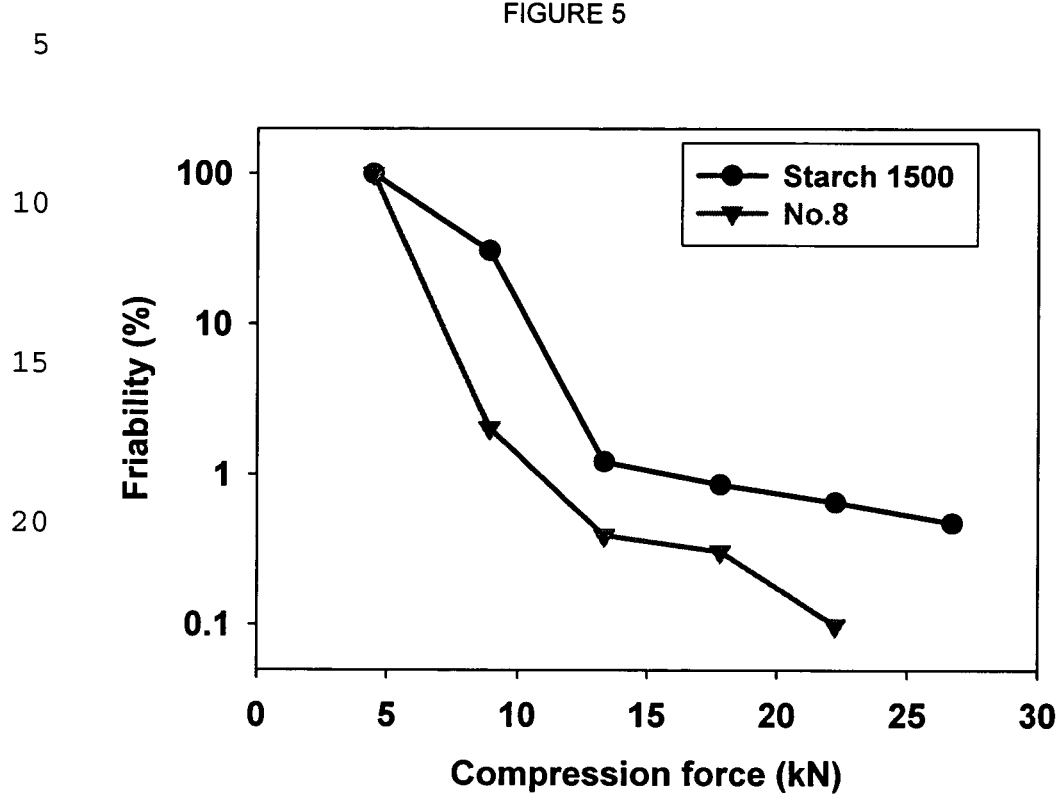
FIG. 5 depicts a friability profile of HCTZ tablets prepared according to Tabletting Procedure 2 using the test defined in the Examples section.

The multi-functional starch composition may be used as a binder, a disintegrant, a filler, or serve the multiple purpose of any combination of these functionalities (e.g. as a binder-disintegrant). The composition has unexpectedly excellent compaction properties resulting in tablet crushing strengths comparable to or better than other starch binders commonly used in the pharmaceutical industry. Thus, the composition advantageously provides binder/filler utility in solid dosage forms, as shown in FIGS. 4 and 5.

Figure 6:
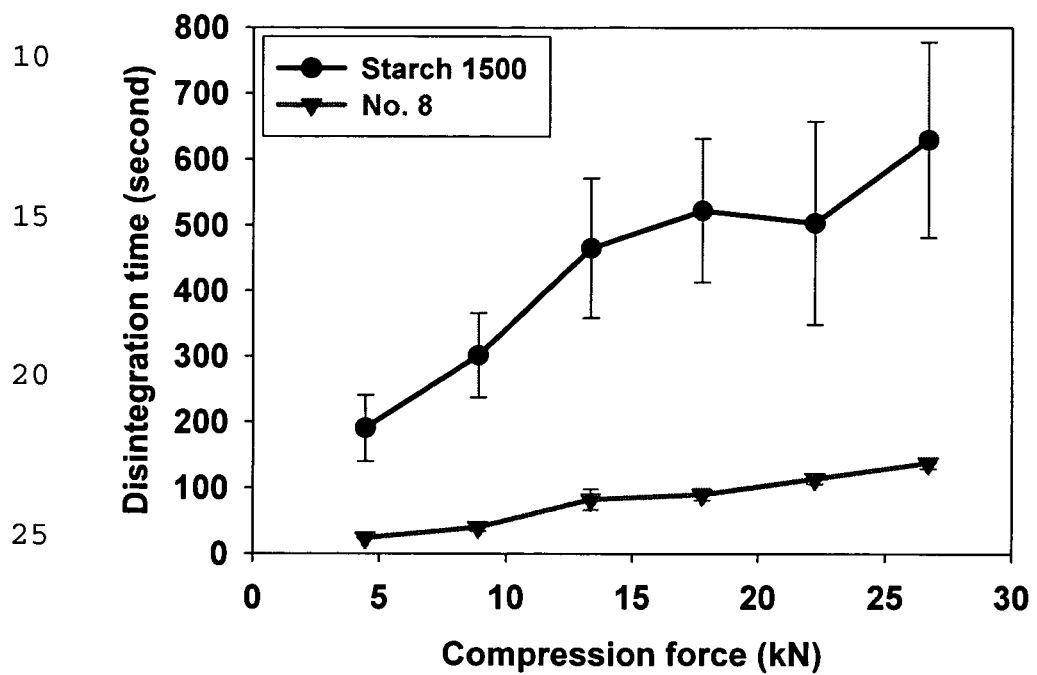
FIG. 6 depicts a disintegration profile of HCTZ tablets prepared according to Tabletting Procedure 2 using the test defined in the Examples section.

The multi-functional starch composition also has excellent disintegration properties, comparable to or better than other starch excipients commonly used in the pharmaceutical industry. The composition advantageously provides disintegrant utility in solid dosage forms, as shown in FIG. 6.

In one embodiment, the composition of this invention is used in conjunction with at least one other excipient in order to manipulate formulation and tablet properties. An effective amount of additional excipient is defined to be the amount of excipient required to confer the desired properties upon the tablet. Still other tablet properties may include, but are not limited to, the desirable degree of tablet crushability, friability, disintegration, dissolution and/or bioavailability.

In another embodiment, optional disintegrants may be used. Said optional disintegrants include, without limit, native starches, modified starches, gums, cellulose derivatives, microcrystalline cellulose, clays, effervescent mixtures and enzymes. The amount of binder (or excipient blend), active ingredient, and lubricant, disintegrant and/or diluent, if any, will depend not only on potency desired, but also on the compatibility of the components and the tablet crushability, friability, disintegrability, dissolution, and/or stability of the final tablet. Anti-adherents, glidants, flavors, coloring agents and the like may also be used. Given the minimum characteristics desired in the final product, the tolerable limits on the weight ratio of the components may be easily determined by the skilled practitioner.

The active ingredients which may be employed herein constitute all active ingredients and include pharmacologically active ingredients, including poorly compressible active ingredients such as, for example, ascorbic acid and ibuprofen. The particular nature of the active ingredient is not critical, however, and also includes non-pharmaceutical active ingredients such as pulverized detergents, dyes, pesticides and food ingredients, including nutritional supplements.

EXAMPLES

The following examples are presented to further illustrate and explain the present invention and should not be taken as limiting in any regard. All percents used are on a dry weight basis. All water used is deionized (DI).

In the examples, the following partially pregelatinized starches disclosed in the prior art were used as a comparison. Starch 1500®, as described in U.S. Pat. No. 4,072,535 is a pre-compacted granular starch powder that obtained by subjecting a non-gelatinized granular starch to physical compaction between steel rollers with the possible input of thermal energy.

C☆ Pharm DC 93000, as described in the U.S. Pat. No. 6,455,069 and U.S. Pat. No. 6,143,324, comprises regular non-birefringent granules of starch and birefringent granules of starch, wherein the ratio of birefringent granules to non-birefringent granules is in the range of from 1:5 to 5:1. The starch powder is obtained by cooking a starch slurry at a temperature not substantially higher than the gelatinization temperature of the starch to cause partial swelling of the starch granules without causing disruption of the starch granules. Then the starch slurry is cooled and spray-dried to produce a starch powder.

LYcatab® C, as described in U.S. Pat. No. 6,184,213, relates to a partially pregelatinized starch containing an effective proportion of intact grains of amylose rich starch enclosed in a pre-gelatinized starch matrix, used as a diluent and disintegrating composition. This composition is prepared by cooking the starch milk of amylose rich starch at a temperature lower than 110° C., followed by drying and grinding.

The following methods and procedures were used to prepare the starches and blends thereof, and include the preparation and evaluation of tablets containing the compressible starch compositions of this invention. The methods and procedures referred to are used throughout the Examples contained herein.

Particle Morphology

The morphology of this partially pregelatinized starch composition was observed using both a microscope and a scanning electron microscope (SEM). For microscopic analysis, approximately 0.5% starch powder was dispersed in water homogeneously and observed using a microscope under both light and polarized light. For SEM analysis, samples were mounted and vacuum-coated with gold. The SEM analysis was performed at 15 kV with a beam current of 2×10−10 A. The distance to sample was set at 15 mm to achieve good image quality.

Particle Size Determination

The particle size and its distribution for the starch powders were measured by Malvern Mastersizer 2000 (Malvern Instruments Ltd., Worcestershire, UK). Approximately 5 ml of powder were used for each measurement. The air pressure was set at 2.0 Bar and the feed rate was set at 50%. The mass median diameter (particle size at which 50% by volume of the sample is smaller and 50% by volume is larger) and particle size distribution were recorded.

Particle Strength Determination

Particle strength was measured by comparing the median particle size of the starch powder that dispersed in water, before and after ultrasonic vibration. The detailed method is described below.

Approximately 0.1 g of starch powder was dispersed in 300 ml DI water which was mechanically agitated and circulated. A laser beam was radiated on the particles suspended in the water and scattered by the particles. The intensity of this scattered light was converted into electrical signals, which were then used to calculate the particle size and distribution. Then ultrasonic vibration was applied to the particle suspension to break apart the agglomerates. The ultrasonic vibration was applied five times for 2 minutes each time. After each ultrasonic vibration, the particle size and distribution were calculated by the intensity of the laser scatter. The particle strength was compared by its size reduction rate during the first 2 minutes of ultrasonic vibration (the fastest size reduction period), which was calculated using the following equation:

$$R = \frac{D_0 - D_t}{2}$$

R=Particle size reduction rate (μm/minute)
$D_0$=Original medium particle size (μm)
$D_t$=Medium particle size after 2 minutes ultrasonic vibration (μm)

Sedimentation Volume (SV)

1.000 grams of starch powder were accurately weighed into a 100 ml graduated cylinder. Approximately 60 ml DI water were added to the starch powder while stirring to make sure it was homogeneously dispersed in water. Then DI water was added again to reach a total of 100 ml volume. The dispersion was undisturbed at room temperature for 24 hours. The total volume of sediment was recorded as sedimentation volume.

Cold Water Solubility (CWS) Determination

An accurately weighed 6.0 grams of starch and 50.0 grams of DI water were placed in a 4 oz jar with a magnetic stirrer. The jar lid was screwed on and the mixture was mixed by shaking for 2 minutes. Then the mixture was filtered through a #2 Whatman filter paper onto a clean Refractometer (0~25%, Fisher, Japan). The reading was multiplied by 9.33 for percent solubility. Two batches per sample were prepared and three reading per batch were analyzed.

Powder Flowability Determination

The flowability of the starch powder was measured using an automated powder flowability analyzer (API Aero-flow™, Amherst Process Instruments Inc., NY). 50 ml starch was placed in a transparent rotating drum, the drum rotation speed was kept constant at 180 rpm. The resultant avalanches were detected by the obscuration of photocells located behind the drum and a two-dimensional strange attractor plot was generated. The average mean time for avalanche (MTA) for three runs was recorded. The smaller the average mean time for avalanche is, the better the powder flowability becomes.

Direct Compression Formulation Blend Preparation

Formulations containing active ingredients were prepared for direct compression. Briefly, the active ingredient, starch composition and other ingredients (except lubricant) were mixed in a Turbula (WAB, Type T2F) mixer for 15 minutes. The mixture is sieved through a 40 mesh (425 μm) sieve and the fraction passing through the screen is used. Lubricant was then added and the blend was mixed for another 1~2 minute. After mixing, the powders are stored in airtight containers until tabletting.

Tabletting Procedures

Procedure 1—Single punch tablet press (Globepharma Model MTCM-1). Placebo starch tablets (containing 100% starch) were produced by this method.

The single station tablet press was fitted with a 1.11 cm (7/16") standard concave punch and a corresponding die. 500 mg of the powder were weighed (1% accuracy) and fed into the die cavity and compressed at 13 kN compression force. The compression time took about two to three seconds.

Procedure 2—Piccola 10-station tablet press. Tablet dosage forms were produced by this method.

The formulation blends containing active ingredients were compressed using an instrumented Piccola 10-station tablet press. Three stations on the tablet press were fitted with a 1.11 cm (7/16") standard concave punch and corresponding die. The tablet weights were adjusted to 500 mg and the tablets compressed at 4, 9, 13, 18, and 22 kN compression forces.

Tablet Hardness Measurements

Tablet hardness, indicated as tablet crushing strength, was determined for ten tablets, prepared according to either Procedure 1 or 2, using a Pharmatron (Model 6D) tablet tester.

Tablet Disintegration Time Measurements

Disintegration times of tablets, prepared according to either Procedure 1 or 2, were determined using an Erweka disintegration tester (Model ZT71, Erweka, Germany). The test was conducted at 37±0.5° C. in a medium of DI water. Six tablets per batch were analyzed.

Dosage Form Drug Dissolution Measurements

The dissolution test was performed on active ingredient containing tablets and hardgel capsules by following respective USP 24 guidelines. A Distek Dissolution Tester (Model Premiere 5100) was used. This equipment was connected to a UV/Vis spectrophotometer (Model HP 8453, Hewlett Packard, Germany) equipped with eight 0.1 cm flow cells, via a 8-channel peristaltic pump (Model HP 89092A, Hewlett Packard, Germany). The percentage of active ingredient released at predetermined time intervals was calculated and plotted against the sampling time to obtain the release profile.

Example 1

Preparation of a Starch Excipient

This example illustrates the preparation of multi-functional starch composition from native corn starch.

Corn starch was extruded on a Werner and Pfleiderer laboratory twin screw extruder (type ZSK-30). The throughput was 10 kg/h. The screw speed was 250 rpm. The screw design consisted of conveying/compression element and one kneading block. The L/d ratio was 9.

The corn starch samples were extruded, at different total moisture contents ranging from 25%-35% and product temperatures ranging from 85-100° C. The SME ranged from 145-210 Wh/kg, using the extruder described above. The composition extrusion conditions are listed in Table 1. The resultant starch compositions were analyzed for sedimentation volume, cold water solubility, mean particle size, flowability, tablet hardness, disintegration time, and moisture content. The results are also reported in Table 1.

TABLE 1

| Samples | Extrudate temperature (° C.) | Total Moisture (%) | SME (Wh/kg) | SV (ml) | CWS (%) | Particle Size (μm) | MTA (second) | Crushing Strength (N) | Disintegration Time (minute) | Moisture Content (%) |
|---|---|---|---|---|---|---|---|---|---|---|
| Native corn starch | | | | 1.0 | 0.5 | 13.5 | 31.4 ± 0.8 | 14.7 ± 1.0 | 0.1 ± 0.0 | 11.4 |
| No. 1 | 85 | 30 | 158 | 6.6 | 4.2 | 69.4 | 7.1 ± 0.2 | 187.3 ± 1.0 | 6.1 ± 0.3 | 8.9 |
| No. 2 | 88 | 32 | 146 | 5.1 | 2.8 | 76.5 | 6.1 ± 0.1 | 181.4 ± 5.9 | 3.4 ± 0.2 | 8.4 |
| No. 3 | 88 | 32 | 146 | 5.0 | 2.7 | 86.9 | 5.5 ± 0.4 | 217.7 ± 3.9 | 2.5 ± 0.2 | 10.0 |
| No. 4 | 93 | 30 | 173 | 6.3 | 4.5 | 58.1 | 7.5 ± 0.1 | 196.1 ± 6.9 | 5.3 ± 0.3 | 8.3 |
| No. 5 | 93 | 35 | 146 | 5.7 | 3.7 | 67.0 | 7.7 ± 0.3 | 179.5 ± 7.8 | 4.0 ± 0.3 | 7.2 |
| No. 6 | 95 | 30 | 180 | 6.9 | 5.6 | 67.5 | 6.1 ± 0.4 | 172.6 ± 8.8 | 7.7 ± 0.3 | 7.0 |
| No. 7 | 100 | 30 | 158 | 7.0 | 5.9 | 79.0 | 6.3 ± 0.3 | 164.8 ± 7.8 | 7.0 ± 0.3 | 7.4 |

Table 1 shows that the extruded starch composition has significantly better flowability than native corn starch, which is indicated by the significantly smaller MTA for extruded starch composition than that for native corn starch. Therefore, the starch composition will be an excellent free flowing direct compression excipient.

As shown in Table 1, the hardness, directly indicated by the crushing strength, of the placebo tablets obtained from the extruded starch composition was significantly higher than that of native corn starch at the same compression force.

Example 2

Preparation of a Starch Excipient

This example illustrates the preparation of multi-functional starch composition from other types of corn starch.

The Werner & Pfleiderer laboratory twin screw extruder (type ZSK-30) was used for the extrusion. The throughput was 10 kg/h. The screw speed was 250 rpm. The screw design consisted of conveying/compression element and one kneading block. The L/d ratio was 9. The total moisture content and product temperatures were controlled around 32% and 88° C., respectively. The SME ranged from 128 to 146 Wh/kg, using the extruder described above. The composition extrusion conditions are listed in Table 2. The resultant starch compositions were analyzed for sedimentation volume, cold water solubility, mean particle size, flowability, tablet hardness, disintegration time, and moisture content. The results are also reported in Table 2.

TABLE 2

| Samples | Extrudate temperature (° C.) | Total Moisture (%) | SME (Wh/kg) | SV (ml) | CWS (%) | Particle Size (μm) | Crushing Strength (N) | Disintegration Time (minute) | Moisture Content (%) |
|---|---|---|---|---|---|---|---|---|---|
| No. 3 | 88 | 32 | 146 | 5.1 | 2.8 | 76.5 | 181.4 ± 5.9 | 3.4 ± 0.2 | 8.4 |
| No. 9a | 88 | 32 | 146 | 5.0 | 2.3 | 93.2 | 171.5 ± 3.0 | 4.8 ± 0.1 | 9.1 |
| No. 10b | 86 | 32 | 128 | 4.9 | 4.2 | 78.5 | 151.9 ± 7.8 | 7.4 ± 0.2 | 8.6 |
| No. 11c | 89 | 32 | 135 | 4.9 | 6.0 | 86.4 | 157.0 ± 3.9 | — | 9.0 |

No. 9 is extruded from 50/50 blend of native/high amylose corn starches
No. 10 is extruded from 50/50 blend of native/waxy corn starches
No. 11 is extruded from waxy corn starch
'—' means the disintegration time is over 2 hours Table 2 shows that, at the same extrusion conditions, an amylose containing starch (e.g., No. 3), and a starch composition with higher amylose contents (e.g., No. 9) provide higher tablet hardness and shorter disintegration time. However, waxy corn starch (No. 11) and a starch composition with high amylopectin contents (No. 10) showed relative low tablet hardness and long disintegration time, within the defined SV and CWS window.

Example 3

Particle Strength of the Starch Excipient

This example evaluates the particle strength of the multi-functional starch composition disclosed in the invention, and compares it with that of other compositions of the prior art.

Sample No. 8 was prepared using the same method as sample No. 2 in Example 1, but at a moisture content of 9.7%. Particle strength of sample No. 8 was measured and compared to that of standard starch excipients used in the art. The results are summarized in Table 3.

TABLE 3

| Samples | Particle Size (μm) | MTA (second) | Particle strength (μm/minute) | Crushing Strength (N) | Disintegration Time (minute) | Moisture Content (%) |
|---|---|---|---|---|---|---|
| No. 8 | 76.5 | 6.1 ± 0.1 | 2 | 214.8 ± 10.8 | 3.8 ± 0.8 | 9.7 |
| C✯ Pharm DC 93000 | 90.6 | 10.7 ± 0.6 | 24 | 175.5 ± 3.9 | 5.9 ± 0.6 | 9.8 |
| Starch 1500 ® | 78.2 | 10.3 ± 0.3 | 47 | 69.6 ± 6.9 | 32.1 ± 9.0 | 10.9 |
| Lycatab ® C | 98.3 | 4.8 ± 0.2 | 2 | 83.4 ± 4.0 | 63.5 ± 1.3 | 9.5 |

C✯ Pharm DC 93000 is prepared as described in U.S. Pat. No. 6,455,069
Starch 1500 ® is prepared as described in U.S. Pat. No. 4,072,535
Lycatab ® C is prepared as described in U.S. Pat. No. 6,184,213

As shown in Table 3, sample No. 8 demonstrates strong particle strength, indicated by the much slower median particle size reduction rate, when compared to C☆ Pharm DC 93000 and Starch 1500®. In fact, the particle size reduction rate of the starch composition according to this invention was very close to that of native corn starch (1 µm/min), which clearly demonstrates that the pregelatinized portion binds the non-pregelatinized portion so strongly that they exist essentially as a single entity. However, weak partial pregelatinized starch agglomerates, such as C☆ Pharm DC 93000 and Starch 1500®, will break down to individual corn granules, with a median particle size decreasing rate of at least 20 µm/min during the first two minute test period. The particle strength study additionally supports the fundamental structure difference between the multi-functional starch composition according to this invention and weak agglomerates of C☆ Pharm DC 93000 and Starch 1500® particle.

Figure 3:
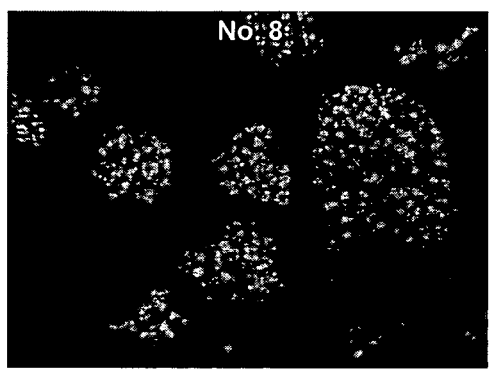
FIG. 3 depicts a photomicrograph taken under polarized light of extruded corn starch, C☆ Pharm DC 93000 as described in U.S. Pat. No. 6,455,069, Starch 1500® as described in U.S. Pat. No. 4,072,535, and Lycatab C as described in U.S. Pat. No. 6,184,213 at a magnification of 200.
Figure 3:
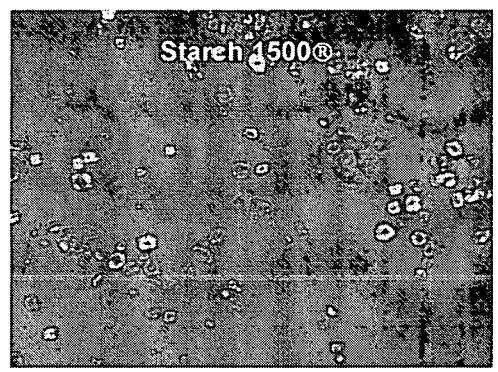
Figure 3:
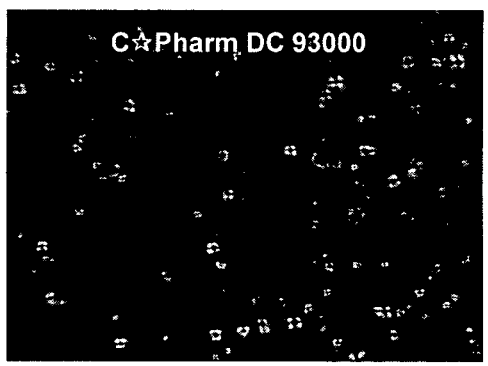
Figure 3:
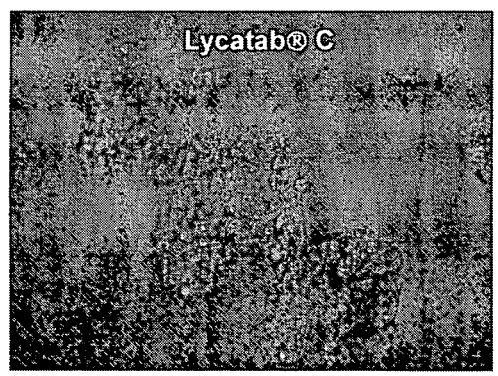

The strong particle strength of the multi-functional starch composition described in this invention is due to the strong binding between non-birefringent portion and birefringent portion. FIG. 3 illustrates the structure of the above four partially pregelatinized starch excipients (Table 3) after they were suspended in water. Most of the weak agglomerates of C☆ Pharm DC 93000 and Starch 1500® were already broke down to individual starch granules, some of the granules lost their birefringence due to pregelatinization. The multi-functional starch composition and Lycatab® C maintained their dry structure without broke down into individual starch granules. In addition, FIG. 3 also clearly indicates the pregelatinization level difference between multi-functional starch composition and Lycatab® C, which results in significant property difference.

The results in Table 3 show that the multi-functional starch composition according to this invention possesses a marked binding and disintegrating function simultaneously, which makes it a good excipient.

Example 4

Preparation of Hard Gel Capsules

This example demonstrates the advantages of the multi-functional starch composition prepared according to Example 1 in hardgel capsules.

In this study, acetaminophen was used as a model active ingredient, and starch was used as a filler and disintegrant in a hardgel capsule formulation.

Acetaminophen (5 grams) and starch (15 grams) were accurately weighed and blended in a Turbular mixer (Glenmills Inc., NJ) for 15 minutes. The comparative starches used were partially pregelatinized starch, native corn starch, waxy corn starch, high amylase corn starch, and fully pregelatinized starch.

Capsule samples were prepared by accurately weighing a 500 mg of acetaminophen/starch mixture and then manually filling the powder into a size 1 gelatin capsule. The acetaminophen release rate was determined as described above. According to USP 25 specification, an immediate release acetaminophen capsule should release not less than 75% acetaminophen in 30 minutes. The percentage of acetaminophen released in 45 minutes and the initial release rate (within 10 minutes) are summarized in Table 4.

TABLE 4

| Capsule sample | % of Acetaminophen released at 45 minute | | | Initial acetaminophen release rate (%/minute) | | |
| --- | --- | --- | --- | --- | --- | --- |
| | 0.1N HCl | pH 4.5 | pH 6.8 | 0.1N HCl | pH 4.5 | pH 6.8 |
| No. 8 | 99.8 | 99.7 | 97.9 | 15.7 | 13.9 | 11.6 |
| C☆ Pharm DC 93000 | 90.1 | 92.4 | 46.8 | 4.4 | 3.7 | 3.6 |
| Starch 1500 ® | 61.2 | 62.8 | 56.1 | 4.5 | 4.3 | 3.7 |
| Lycatab ® C | 96.8 | 97.6 | 92.7 | 11.4 | 10.6 | 9.2 |
| Native corn starch | 95.9 | 91.2 | 91.8 | 7.0 | 5.4 | 5.4 |
| Waxy corn starch | 96.2 | 97.8 | 87.1 | 5.8 | 5.5 | 5.4 |
| High amylase corn starch | 95.6 | 91.7 | 93.8 | 5.8 | 3.7 | 3.5 |
| Fully pregelatinized corn starch | 48.1 | 44.2 | 29.3 | 1.9 | 1.9 | 0.9 |

Table 4 clearly shows that the multi-functional starch composition disclosed in this invention provides the fastest acetaminophen release. The burst drug releasing power (initial drug release rate) of the formulation containing the starch of the present invention was greater than that of the comparative starches. This is indicative of a significant advantage over other existing starch compositions when used as a filler/diluent in immediate release capsule type dosage forms.

Example 5

Preparation of HCTZ Tablets

This example demonstrates the advantages of the multi-functional starch composition prepared according to Example 1 in hydrochlorothiazide (HCTZ) tablets. Starch 1500® was used as a comparison.

Formulation blends were prepared as describe in the direct compression formulation blend preparation section and tabletted according to Tabletting Procedure 2. Either sample No. 8 or Starch 1500® were used as the starch using the formulation of Table 5.

TABLE 5

| Ingredients | Functions | Weight (%) |
| --- | --- | --- |
| Hydrochlorothiazide | Active | 25 |
| Starch | Binder/disintegrant | 74.8 |
| Magnesium stearate | Lubricant | 0.2 |

FIG. 4 shows that the hardness of HCTZ tablets containing the multi-functional starch composition was much higher than that of Starch 1500® at any compression force. In corresponding to a harder tablet, the HCTZ tablet containing the multi-functional starch composition was much less friable at commonly used compression forces than that containing Starch 1500® (as shown in FIG. 5. Due to the high binding capability of the multi-functional starch composition, tablets could be manufactured at lower compression forces, yet similar hardness could be obtained. This is a significant advantage in the course of the tabletting process.

Figure 7:
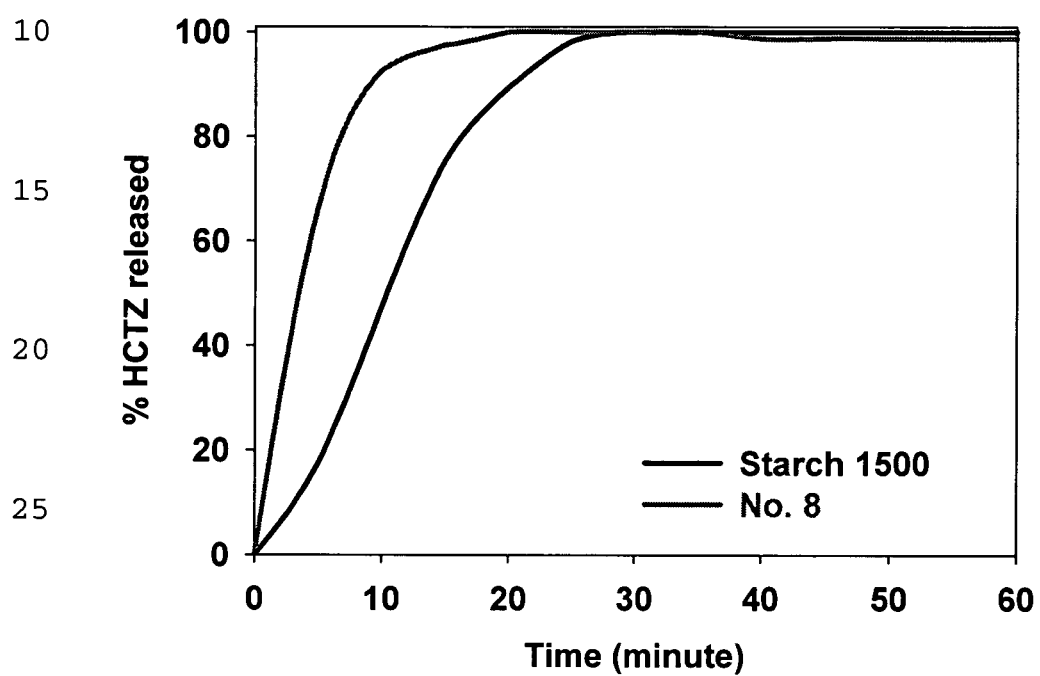
FIG. 7 depicts a dissolution profile of HCTZ tablets prepared according to Tableletting Procedure 2 using the test defined in the Examples section.

FIG. 6 displays the superior tablet disintegration rate of HCTZ tablets containing the multi-functional starch composition. At any compression force, the multi-functional starch composition always disintegrates the tablets at a much faster rate than Starch 1500®. As a result of fast disintegration, the HCTZ release from the multi-functional starch composition containing tablets was much faster than from Starch 1500® containing tablets, as shown in FIG. 7. Another factor that contributed to the different dissolution rate was the disintegration pattern. The multi-functional starch composition containing tablets disintegrated to fine powders, and the active ingredient could be released immediately. However, the Starch 1500® containing tablets disintegrated to coarse fragments, which prevented ready release of the active ingredient.

We claim:

1. A solid dosage form comprising an extruded partially pregelatinized starch characterized by:
    a) a plurality of particles, a majority consisting of a non-birefringent portion and a birefringent portion;
    b) a sedimentation volume of between 1.5 and 9 ml/g;
    c) a cold water solubility of between 1 and 8%; and
    d) an average particle size between 40 and 150 microns;
    e) wherein, when the starch is used to prepare a placebo starch tablet consisting of the starch, the placebo starch tablet is characterized by at least the following:
        i) a crushing strength of at least 160 N; and
        ii) a disintegration time of no more than 10 minutes.

2. The solid dosage form of claim 1, wherein the sedimentation volume is between 3 and 6 ml/g.

3. The solid dosage form of claim 1, wherein the cold water solubility is between 2 and 5%.

4. The solid dosage form of claim 1, wherein the average particle size is between 60 and 100 pm.

5. The solid dosage form of claim 1, wherein the starch has a moisture content of from 5 to 12% by weight.

6. The solid dosage form of claim 1, wherein the starch has a moisture content of between 8 and 10%.

7. The solid dosage form of claim 1, wherein the starch has a mean time for avalanche of no more than 10 seconds.

8. The solid dosage form of claim 1, wherein the starch has a mean time for avalanche of no more than 7 seconds.

9. The solid dosage form of claim 1, wherein the starch is further characterized by a particle strength of about 2 pm/min.

10. The solid dosage form of claim 1, wherein the dosage form is selected from the group consisting of tablets, caplets, powders and dry dosage capsules.

11. The solid dosage form of claim 10, wherein the dosage form is a tablet.

12. The tablet of claim 11, wherein the tablet has a moisture content of at least 7%.

13. The tablet of claim 12, wherein the tablet has a crushing strength of at least 180 Newtons.

14. The tablet of claim 12, wherein the tablet has a crushing strength of at least 200 Newtons.

15. The tablet of claim 12, wherein the tablet has a disintegration time of no more than 8 minutes.

16. The tablet of claim 12, wherein the tablet has a disintegration time of no more than 5 minutes.

* * * * *